United States Patent [19]
Bes et al.

[11] Patent Number: 6,027,012
[45] Date of Patent: Feb. 22, 2000

[54] METHOD FOR MAKING METAL FRAMEWORKS FOR DENTAL PROTHESES

[76] Inventors: Claude Bes, 4, Allée, F-34670 Baillargues; Claude Segura, 20 Rue Claude Bernard, F-66000 Perpignan, both of France

[21] Appl. No.: 09/042,304

[22] Filed: Mar. 13, 1998

Related U.S. Application Data

[63] Continuation-in-part of application No. PCT/FR96/01403, Sep. 12, 1996.
[51] Int. Cl.⁷ .................................................... B23K 31/02
[52] U.S. Cl. ........................ 228/175; 228/226; 228/248.5; 433/206
[58] Field of Search ..................................... 228/175, 226, 228/248.5; 433/201.1, 206, 207, 208; 419/8, 9, 26

[56] References Cited

U.S. PATENT DOCUMENTS

| | | | |
|---|---|---|---|
| 4,077,560 | 3/1978 | Sung et al. ................................ | 228/220 |
| 4,426,404 | 1/1984 | Shoher et al. ........................... | 228/209 |
| 4,938,409 | 7/1990 | Roberts .................................... | 228/178 |
| 5,909,612 | 6/1999 | Zel ............................................ | 419/5 |

FOREIGN PATENT DOCUMENTS

| | | |
|---|---|---|
| 0 104 320 | 4/1984 | European Pat. Off. . |
| 0 464 951 | 1/1992 | European Pat. Off. . |
| 2 660 224 | 10/1991 | France . |

*Primary Examiner*—Samuel M. Heinrich
*Attorney, Agent, or Firm*—Graybeal Jackson Haley LLP

[57] ABSTRACT

The present invention relates to a method for making metal frameworks for dental protheses:

of the type comprising metallic cops, optionally coated with resin or ceramic material, designed to be anchored in the mouth directly onto the stump of the tooth or teeth to be restored, contiguous or independent, optionally coupled by also metal intermediate members;

using for the embodiment of said cops directly on the master mould, generally of plaster, obtained from the patient maxilla or mandibular cast, i.e. without having to pass through a duplicate in refractory material, first a thin metal sheet forming operation on the stump model of the tooth to be restored and then wintering and/or melting operation of precious, semiprecious and non-precious metal powder, coating said metal sheet, through the effect of a suitable heat supply.

8 Claims, No Drawings

METHOD FOR MAKING METAL FRAMEWORKS FOR DENTAL PROTHESES

This is a Continuation-in-Part of co-pending International Application PCT/FR96/01403 filed on Sep. 12, 1996 designating the United States.

BACKGROUND OF THE INVENTION

1. Field of the Invention

The present invention relates to a method for making metal frameworks for dental protheses:

- of the type comprising metallic cops, optionally coated with resin or ceramic materials designed to be anchored in the mouth directly onto the stump of the tooth or teeth to be restored, contiguous or independent, optionally coupled by also metal intermediate members;
- using for the embodiment of said cops directly on the master mould, generally of plaster, obtained from the patient maxilla or mandibular cast, i.e. without having to pass through a duplicate in refractory material, first a thin metal sheet forming operation on the stump model of the tooth to be restored and then sintering and/or melting operation of precious, semiprecious and non-precious metal powder, coating said metal sheet, through the effect of a suitable heat supply.

2. Description of Related Art

Just now the most spread technique in the field of making metal copings for dental protheses is the so-called lost wax process which consists, successively in making the cop (or framework) wax pattern on the master model; to place said pattern in a cylinder (with refractory coating); to locate the assembly in a heating oven to make the wax melt; to cast (in an electronic splint) melt metal (generally a nickel-chromium alloy) which is going to occupy the whole volume left by the wax; to adjust (scraping and sand blasting) the cop achieved.

Above technique shows following drawbacks:

- time for making a cop is about 3 hours (cylinder hardening, temperature raising and cooling . . . times).
- the material is used in large amounts (overall significant when using precious metals) because cop thickness is at least 0.6 mm with more loss associated to the requirement to forecast casting shafts and several reservations;
- the quality of the cop achieved requires a significant adjustment work (porousness because of the gas released during casting, suppression of casting shafts . . . ).

The prior art closest to the technique according to the invention is disclosed in the document FR-A-2660224 (of same applicants) which consists first in forming a 0.02 to 0.03 mm metal sheet on the model involved, then to sprinkle a base metal powder on said sheet so formed previously coated with binding substance, then to coat said particles with a filler metal having a melting point lower than that of the base metal, by Electrodeposition, by metal sublimation or by plasma projection, then to raise the temperature to get binding between filler metal particles and base metal particles, in order to separate the metal sheet from the overlying metal framework so achieved.

The technique involved, which in still at the experimental stage, shows following drawbacks:

- to achieve cops having required mechanical qualities, several layers of base metal are required (because it has to be present in larger amounts than the filler metal) and each time a layer of binding material therefore oxidation problems when melting it;
- the layers so obtained does not stand the electrolytic bath (stirrer and temperature);
- the interpenetration does not occur in good conditions when melting, therefore homogeneity problems arise in the cops obtained;
- it is very hard to separate in good conditions the metal sheet/melt cop;
- the classical type binding material does not allow to reduce oxidation;
- retraction phenomena of melt metal modify size characteristics of the cops obtained.

SUMMARY OF THE DISCLOSURE

The inventors have conducted searches to achieve a technique adapted to meet the technical and economic demands linked to dental art which essentially consisted in:

- directly working on the master model suppressing the step of making a duplicate which is long and expensive;
- using sintering and melting techniques of metal alloy powders which allow to obtain half thinner cops (0.3 mm as an average), which means to make economically possible to use semiprecious and precious metals and having a very best aesthetics (suppressing the palatal band);
- finding solutions which overcome the problems associated to oxidation, retraction, heterogeneity phenomena of metal sheets: obtained . . .
- suppressing adjustment step (namely, scrapping);
- working either with non-precious, semiprecious or precious metals.

The process according to the invention allows making a metal sheet in less than 15 minutes compared against 3 hours with the base technique the so-called lost wax process and meeting several technical and economical demands associated to the dental art.

The characteristics and advantages of the invention will become clearly apparent from the detailed description below of a preferred embodiment of the invention with several variants, given for non-limitative example purpose.

DETAILED DESCRIPTION OF THE PREFERRED EMBODIMENTS

The process according to the invention essentially consists in:

- directly coating the stump of the master model corresponding to the tooth to be restored, with a film of binding substance which has the property on one hand to keep the metal sheet binds against said stump when forming it and on the other hand to volatilize under the effect of a suitable heat supply so that it allows the metal sheet bearing the metallic powder onto it is taken apart from said stump before the cop proper forming operation under the effect of the suitable heat supply;
- using, to coat said stump model, in turn coated with said binding substance film, with a metal sheet the melting point of which is higher than the melting point of the metal particles of the metal powder designed to melt during cop forming operation under the effect of the suitable heat supply and which has the property not to form, at forming temperature of said cop, an eutectic mixture with one or several of the metal constituents of said metal powder;

using, to coat said metal sheet formed on said stump model, a metal powder of which one part of the metal a particles has the property to melt at the temperature of transforming the cop proper so that on one hand to weld between them the other portion of the metal particles which did not melt at said temperature and on the other hand to weld the overlying cop which is being formed onto the underlaying cop constituted by the metal sheet formed on said model of stump;

to submit then the assembly constituted by the metal sheet, coated with metal powder to the action of the suitable heat supply so that a monolithic composed cop is obtained constituted by the coat of overlying metal powder integral with the underlying metallic sheet.

According to a variant of the invention, the process consists in:

a) coating the internal part of the metal sheet, taken apart from the master model and coated with metal powder, before submitting said assembly to the effect of the suitable heat supply, with a pasty mixture obtained from a powder refractory product and a liquid binding material;

b) to remove, after making the composed cop, the layer of refractory product it contains.

The binding substance coating the stump model allows to prevent bad contacts between the metal sheet to be formed and said model, overall with the use of sheet having a thickness under 0.010 mm where microhammering is not necessary (gain of time, better forming, microhammering device saving). In addition, with the metal sheets having a thickness over 0.010 mm, hand pre-forming of theses later is essential.

The eutectic mixture which could be formed between the metal sheet and the metal powder would have as effect to have this sheet essentially melting with sheets having a thickness under 0.010 mm.

The use of a refractory mixture within the cop taken apart from the master model has the effect of making said cop stiff on one hand to handle it without deforming it and on the other hand to serve as melting support. The refractory mixture is prepared in less than one minute and it is spread within the cop with a simple brush.

The metal sheet used serves essentially as:

mechanical insulation with respect to the support when mounting the powder;

contact plain surface with respect to the stump of the tooth to be restored;

mechanical insulation with respect to the refractory coating which could penetrate within the interstices of the powder should the sheet do not exist;

mounting support for the metal powder and mechanical insulation with respect to this later which could penetrate within the porosities of the support when it is formed under the effect of the suitable heat supply.

In the event of using non-precious alloy powders (nickel-chromium or chromium cobalt, for example), a compatible metal powder, according to the atomic attraction phenomenon, with at least one of its constituents of metal alloy, can be mixed to the refractory product (best behavior of the metal particles when forming the cop).

The metal sheet, formed on the stump model, can be coated with a film of calcinable binding substance adapted to bind, before mounting the overlying cop proper, a film of metal powder of the type used to make said cop. This operation allows creating a rough surface which contributes to beat mounting the pasty metal sheet (best keeping) on the metal sheet. Above pasty mixture comprises the metal powder and a liquid binding material (binding material in suspension in a solvent).

The liquid binding material used is advantageously made from a mixture of powder polyvinylpyrrolidone, water, methanol and/or ketone ratably for obtaining, when it is mixed with thus metal alloy powder, a pasty product the consistence of which allows its mounting on the formed metal sheet.

Preferred percentages (in volume) are as follows:

| | |
|---|---|
| polyvinylpyrrolidone: | 20 to 40% |
| water: | 20 to 35% |
| methanol: | 20 to 35% |
| ketone: | 20 to 35% |

The water acts as an evaporation moderator and the ketone (and/or methanol) as an evaporation accelerator. The mixture was defined to take into account a consistence adapted to an easy assembly during all the work and evaporation time when ending the assembly (drying under the effect of a suitable heat supply).

The overlying cop can be made of two powder metal alloys having different melting points.

The two alloys can be:

either mixed at same time to same binding material to constitute a single pasty mixture;

or separately mixed to same binding material to constitute two pasty mixtures which will be applied in superimposed layers, the one having the highest melting point first.

The base metal layer which possesses the highest melting point, can also be placed between filler metal layers having the lowest melting point. When melting occurs, there is an interpenetration, by capillarity and by atomic attraction, of the two external layers melting within the base metal mass.

According to a variant of the invention, when using non-precious alloys, the lowest melting point of the alloy is that of nickel-chromium and the highest melting point is that of chromium-cobalt; the former having, for example a melting point of 1100° C. and the later of 1200° C. The metal sheet used can in this case be platinum.

The composition of these different alloys, which are of the type used in dental protheses, is for example:

for nickel-chromium: 70–75% nickel to 25–30% chromium;

for chromium-cobalt: 25–30% chromium to 70–75% cobalt.

The ratio of theses different alloys in the end composition is for example 15–30% of nickel-chromium (which constitutes the filler metal) to 70–85 chromium-cobalt (which constitutes the base metal).

The metal obtained after melting includes a percentage of nickel lower than 15% therefore under toxicity threshold.

In the event of using these alloys, the metal powder mixed with the refractory powder (which can be pure alumina) is for example nickel.

In the event of another variant of the invention, when using semiprecious alloys, alloys used can be based on palladium and gold and in variable ratios in order to obtain alloys having different melting points as for example 1100° C. for the less palladium dosed alloy and 1300° C. for the most palladium dosed and having a granulometry ranging for example from 0.02 to 0.06 mm.

Alloys having different granulometries can also be used to make same cop. In this case the alloy having the lowest granulometry falls on the lowest melting point and constitutes the filler metal the particles of which when melting are going to weld the particles of the other alloy.

Weldings can be carried out from an alloy having same nature with a higher dose of gold.

In a more extended way, the granulometry of metal powders can advantageously range from 0.01 to 0.1 mm.

In the different metal alloys which can be used in powder:

palladium provides stiffness and increases the melting point;

silver can provide an easier bond and platinum can raise the melting point;

chromium provides stiffness, boron can provide melting point lowering, copper provides hardness and silicon is a deoxidizer.

The bond (affinity) between the different particles of the metals used provides phenomena associated to:

attraction of particles having the highest melting point with respect to particles having the lowest melting point;

capillarity of the alloy melting within non-melt allow recesses;

adsorption and surface tension of the metal particles;

different granulometries of the particles present with each other;

The retraction phenomenon of the cop when forming is also removed.

The alumina used as refractory powder has also a deoxidizing power.

It is also possible to coat the cop obtained, in the event of using non-precious metal alloys, with a precious (or semiprecious) alloy or metal layer.

To decrease oxidation phenomenon associated to every metal (mainly non-precious) powder melting, melting cycle can be performed in a deoxidizing atmosphere.

The metal sheet used can advantageously have a thickness less than 0.01 mm. Namely, a 0.005 mm sheet is formed on the stump in loss than one minute with a simple brush and the binding substance is essential in this case.

The metal sheets obtained can be associated to intermediate metal elements;

b) by providing a metal powder pasty mixture, of above type but having a lower melting point, so that to provide said intermediate elements with the wished end shape and to secure, through melting, interstice binding;

c) under the action of a suitable heat supply on the assembly so obtained, taken apart from the master model until melting the metal powder pasty mixture used.

The binding material used with the refractory product (pure alumina for example) can be of same type as the one used with metal powders.

Obviously, the invention it not limited to the embodiments disclosed for which other variants can be provided in:

the nature of the materials used;

the melting temperature, the granulometries, the compositions and the percentages of the metal alloys included in the composition of the cop;

the thicknesses and the nature of the metal sheets used;

the heat supplies used (Bunsen burner, blowlamp, resistor, induction, infrared radiation heating oven . . . ); and to extend it to other applications;

without being out of the scope of the invention.

We claim:

1. A method for making metal frameworks for dental protheses:

of the type comprising metallic cops, optionally coated with resin or ceramic material, designed to be anchored in the mouth directly onto the stump of the tooth or teeth to be restored, contiguous or independent, optionally coupled by also metal intermediate members;

using for the embodiment of said cops directly on the master mould, generally of plaster, obtained from the patient maxilla or mandibular cast, i.e. without having to pass through a duplicate in refractory material, first a thin metal sheet forming operation on the stump model of the tooth to be restored and then sintering and/or melting operation of precious, semiprecious and non-precious metal powder, coating said metal sheet, through the effect of a suitable heat supply;

using metallic powders having different melting points in order to weld among they the particles having a high melting point with the particles with a lower melting point; wherein said method consists in:

(a) directly coating the stump of the master model corresponding to the tooth to be restored, with a film of binding substance which has the property on one hand to keep the metal sheet secured against said stump when forming it and on the other hand to volatilize under the effect of a suitable heat supply so that it allows the metal sheet bearing the metallic powder onto to be taken apart from said stump before the cop proper forming operation under the effect of the suitable heat supply;

(b) using, to coat said stump model, in turn coated with said binding substance film, a metal sheet the melting point of which is higher than the melting point of the metal particles of the metal powder designed to melt during cop forming operation under the effect of the suitable heat supply and which has the property not to form, at forming temperature of said cop, an eutectic mixture with one or several of the metal constituents of said metal powder;

(c) using, to coat said metal sheet formed on said stump model, a metal powder of which one part of the metal particles has the property to melt at the temperature of transforming the cop proper so that on one hand to weld between them the other portion of the metal particles which did not melt at said temperature and on the other hand to weld the overlying cop which is being formed onto the underlying cop constituted by the metal sheet formed on said model of stump;

(d) to submit then the assembly constituted by the metal sheet, coated with metal powder to the action of the suitable heat supply so that a monolithic composed cop is obtained constituted by the coat of overlying metal powder integral with the underlying metallic sheet.

2. A method as recited in claim 1, wherein it comprises:

(a1) coating the internal part of the metal sheet, taken apart from the master model and coated with metal powder, before submitting said assembly to the effect of the suitable heat supply, with a pasty mixture obtained from a powder refractory product and a liquid binding material;

(b1) removing, after making the composed cop, the layer of refractory product it contains.

3. A method as recited in claim 1, wherein the particles having a different melting point belong to two metallic alloys with are mixed at the same time to same binding material to constitute a single pasty mixture.

4. A method as recited in claim 1, wherein the particles having a different melting point belong to two metallic alloys with are separately mixed to same binding material to constitute two pasty mixtures which will be applied in superimposed layers, the one having the highest melting point first.

5. A method as recited in claim 1, wherein said metallic sheet has a thickness less than 0.01 mm.

6. A method as recited in claim 1 wherein the granulometry of metal powders can advantageously range from 0.01 to 0.1 mm.

7. A method as recited in claim 1 wherein the liquid binding material used is made from a mixture of powder polyvinylpyrrolidone, water, methanol and/or ketone ratably for obtaining, when it is mixed with the metal alloy powder, a pasty product the consistence of which allows its mounting on the formed stump mould.

8. A method as recited in claim 1 wherein the metal sheets obtained are associated to intermediate metal elements;

a) by electric spot welding acting directly on the master mould;

b) by providing a metal powder pasty mixture, of above type but having a lower melting point, so that to provide said intermediate elements with the wished end shape and to secure, through melting, interstice binding;

c) under the action of a suitable heat supply on the assembly so obtained, taken apart from the master model until melting the metal powder pasty mixture used.

\* \* \* \* \*